US008621489B2

(12) United States Patent
McQuaid et al.

(10) Patent No.: US 8,621,489 B2
(45) Date of Patent: Dec. 31, 2013

(54) UNIVERSAL MEDICAL DEVICE DRIVER ADAPTER

(75) Inventors: William C. McQuaid, Melrose, MA (US); Thomas J. Botzer, Bethel Park, PA (US)

(73) Assignee: Koninklijke Philips N.V., Eindhoven (NL)

( * ) Notice: Subject to any disclaimer, the term of this patent is extended or adjusted under 35 U.S.C. 154(b) by 15 days.

(21) Appl. No.: 13/510,973

(22) PCT Filed: Nov. 18, 2010

(86) PCT No.: PCT/IB2010/055270
§ 371 (c)(1),
(2), (4) Date: May 21, 2012

(87) PCT Pub. No.: WO2011/073822
PCT Pub. Date: Jun. 23, 2011

(65) Prior Publication Data
US 2012/0284734 A1 Nov. 8, 2012

Related U.S. Application Data

(60) Provisional application No. 61/287,014, filed on Dec. 16, 2009.

(51) Int. Cl.
*G06F 13/10* (2006.01)
(52) U.S. Cl.
USPC .......................................... 719/327; 719/321
(58) Field of Classification Search
CPC .................................................... G06F 13/102
USPC .................... 719/327, 321; 717/100
See application file for complete search history.

(56) References Cited

U.S. PATENT DOCUMENTS

| 2003/0120624 | A1* | 6/2003 | Poppenga et al. | 707/1 |
| 2004/0221298 | A1* | 11/2004 | Cedola | 719/321 |
| 2005/0198236 | A1* | 9/2005 | Byers et al. | 709/222 |
| 2006/0069452 | A1 | 3/2006 | Pfister et al. | |
| 2007/0213598 | A1* | 9/2007 | Howard et al. | 600/300 |

(Continued)

FOREIGN PATENT DOCUMENTS

EP 1603038 A2 12/2005
EP 1643679 A1 4/2006

OTHER PUBLICATIONS

Danmeter, "Cerebral State Monitor (CSM) Connectivity to Patient Monitors Supporting VueLink Open Interface," (Mar. 13, 2006) [retrieved from www.danmeter.dk/products/neuromonitoring/csm-monitor/posters_brochures/Factsheet%20for%20CSM%20Philips%20VueLink.pdf].*

(Continued)

*Primary Examiner* — H S Sough
*Assistant Examiner* — Brian W Wathen

(57) ABSTRACT

A universal medical device driver adapter that enables the creation of medical device drivers without the need to write custom software for typical medical devices, thereby reducing development time for individual drivers and reducing training time and skill sets requirements of driver developers. Various format parameters are defined, such as baud rate, parity, buffer size, time stamps, tokens, message link, and the like, in an XML device driver file. When a recognized medical device is specified, the corresponding XML file is retrieved and an interface uses the parameters described therein for bidirectional communication with the monitor.

17 Claims, 15 Drawing Sheets

(56) References Cited

U.S. PATENT DOCUMENTS

| | | | |
|---|---|---|---|
| 2007/0245345 A1* | 10/2007 | Yamada | 717/174 |
| 2008/0046292 A1* | 2/2008 | Myers et al. | 705/3 |
| 2009/0036750 A1* | 2/2009 | Weinstein et al. | 600/300 |
| 2009/0064196 A1 | 3/2009 | Richardson et al. | |
| 2009/0228623 A1* | 9/2009 | Tsuchiya | 710/72 |
| 2009/0240526 A1* | 9/2009 | Vesto et al. | 705/3 |
| 2009/0287863 A1* | 11/2009 | Robertson et al. | 710/64 |
| 2010/0161354 A1* | 6/2010 | Lim et al. | 705/3 |
| 2010/0318699 A1* | 12/2010 | Gao-Saari et al. | 710/72 |

OTHER PUBLICATIONS

Choi, Y.H.; Kwon, W.; Kim, H.N, "Code generation for Linux device driver," The 8th International Conference on Advanced Communication Technology (Feb. 20-22, 2006), pp. 734-737 [retrieved from http://ieeexplore.ieee.org/stamp/stamp.jsp?tp=&arnumber=1625675&isnumber=34120].*

* cited by examiner

US 8,621,489 B2

UNIVERSAL MEDICAL DEVICE DRIVER ADAPTER

CROSS REFERENCE TO RELATED APPLICATIONS

This application claims the benefit of U.S. provisional application Ser. No. 61/287,014 filed Dec. 16, 2009, which is incorporated herein by reference.

The present application finds particular utility in hospital information systems (HIS). However, it will be appreciated that the described technique(s) may also find application in other types of medical systems, other device driver systems, and/or other device communication frameworks.

Philips' IntelliBridge™ platform consists of various components that combine to create a medical device interfacing solution for Philips products. The EC10, EC40, and EC80 communication platforms are Linux based platforms that physically connect to a medical device, communicate and obtain data through the use of drivers, convert the data to a standard 11073 format, and deliver the data to a central server. The EC10 provides data to Philips brand monitors exclusively, while the EC40/80 provides data to hospital information systems (HIS) via an SC50 communication architecture.

EC10 is a replacement for an existing solution and can reside on an existing installation with the legacy solution. If a given device driver has not yet been developed for the EC10, the legacy solution can be used. Unlike the EC10, the EC40/80 cannot co-exist with the legacy solution, so if a driver does not exist for an EC40/80, it needs to be developed.

There is an unmet need in the art for systems and methods that facilitate providing a stream-lined approach for developing a large library of medical device drivers, and the like, thereby overcoming the deficiencies noted above.

In accordance with one aspect, a system that facilitates providing reusable code for device drivers in an expandable and scalable framework includes a multi-port medical data acquisition device (MDAD) that detects a medical device coupled to the MDAD via a single port pass-through connection, and a device driver manager (DDM) tool that generates a plug-and-play extensible markup language (XML) device driver file for the medical device. The system further includes a computer-readable medium that stores the XML device driver file for use whenever the medical device or a similar device is coupled to the system. The XML device driver file includes a plurality of format parameters descriptive of a device driver for the medical device.

In accordance with another aspect, a method of generating reusable extensible markup language (XML) device driver files includes selecting a device driver from a list of device drivers, configuring an XML device driver file for the selected device driver using a device driver manager (DDM) tool, and generating the XML device driver file when it is completely configured. The method further includes storing the XML device driver file to a computer-readable medium for recall upon detection of a compatible medical device. The XML device driver file includes a plurality of format parameters descriptive of a device driver for the medical device.

In accordance with another aspect, an extensible markup language (XML) device driver manager (DMM) tool includes a user interface that includes a plurality of selectable buttons and text fields by which a user enters information and configures an XML device driver file for a medical device. The information includes one or more driver properties, one or more message properties, one or more driver parameters, and one or more stripping elements.

One advantage is that device driver time to market is reduced.

Another advantage resides in reduced development cost per driver.

Another advantage resides in reduced training time and skill set requirements for driver developers.

Another advantage resides in minimizing lines of code per driver.

Another advantage resides in minimizing driver maintenance costs

Another advantage resides in facilitating standardization initiatives.

Still further advantages of the subject innovation will be appreciated by those of ordinary skill in the art upon reading and understand the following detailed description.

The drawings are only for purposes of illustrating various aspects and are not to be construed as limiting.

Figure 1:
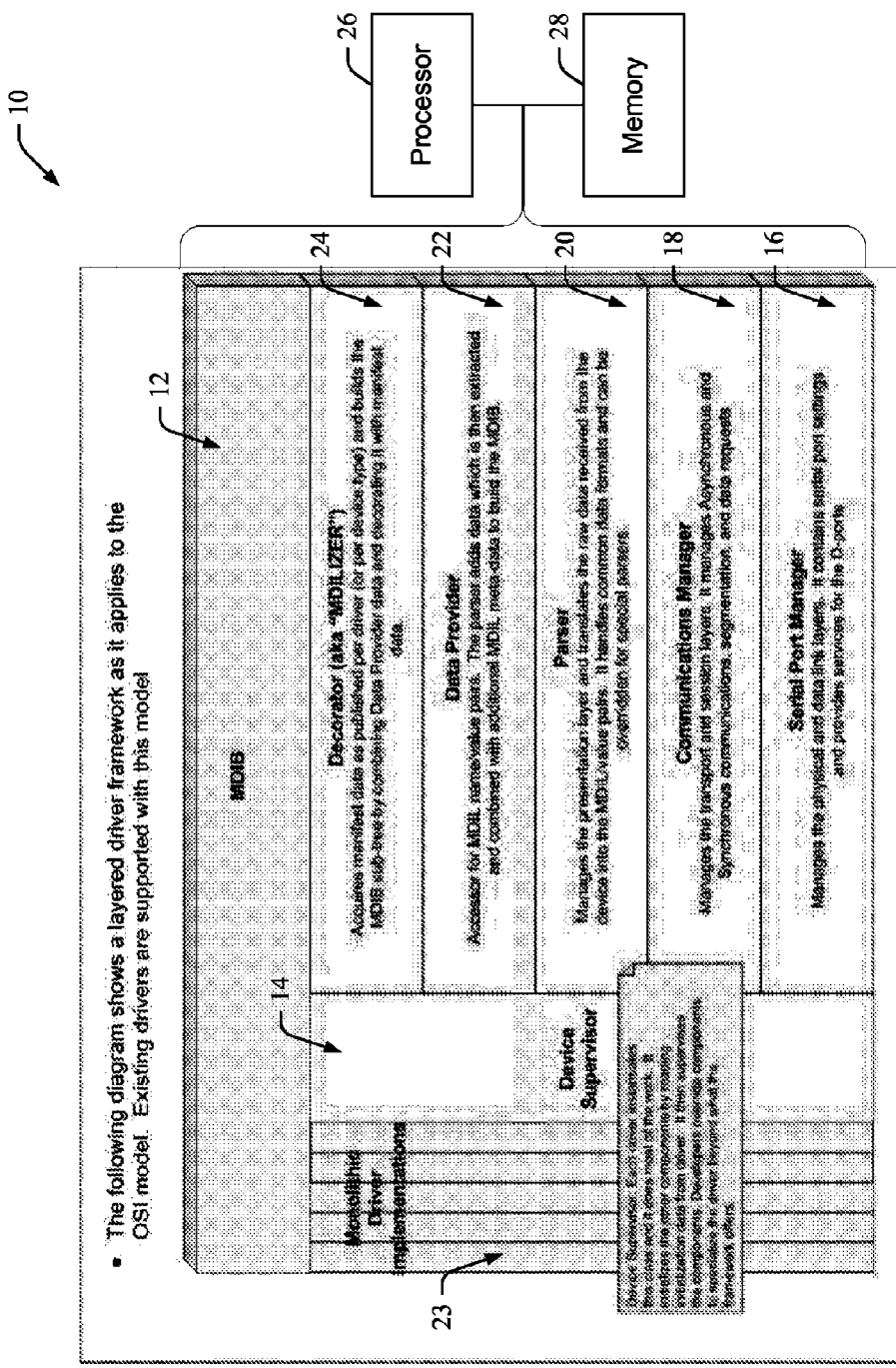
FIG. 1 illustrates a universal medical device driver adapter (UMDAA) system or framework that facilitates minimizing an amount of code used for device drivers in a plug-and-play medical device environment.

FIG. 1 illustrates a universal medical device driver adapter (UMDAA) system or framework 10 that facilitates minimizing an amount of code used for device drivers in a plug-and-play medical device environment. The system 10 includes an medical data information base (e.g., a database) (MDIB) 12 that comprises an object-oriented configurable framework that is capable of retrieving medical device metrics or parameters from medical devices such as ventilators, anesthesia devices, and infusion pumps, and the like, using various proprietary (vendor specified) protocols and converts the metrics into a normalized data representation. External applications can access the normalized data through an interface for the purpose of converting the metrics to protocols including, but not limited to 11073 (medical data information language, or "MDIL") and HL7 protocols.

The UMDDA 10 comprises a device supervisor component 14 that dynamically configures framework components according to the make/model of the medical device for which a drive is to be generated by selecting the appropriate extensible markup language (XML) configuration file per medical device. For example, the supervisor 14 can be configured to "listen" for plug and play events and dynamically select the appropriate XML file to communicate with a specific device. It is the job of the device supervisor model to configure a port manager 16, communications manager 18, parser 20, and data provider 22 for use with a specified device model. The port manager, communications manager, parser and data provider encapsulate layers of an open system interoperability (OSI) model and interoperate for the purpose of providing the full medical device driver functionality.

The port manager 16 manages the physical and data link layers of the communications stack. For example, this layer can be used to configure serial port settings such as baud rate, stop bits, and parity. The communications manager 18 controls the transport and session layers. It manages asynchronous and synchronous communications, message segmentation, and data requests. The parser 20 manages the presentation layer and translates raw data received from the device into the normalized parameter ID/value pairs. There are several patterns implemented in the parser layer such as "fixed buffer" parsers and different types of "tagged data parsers". This layer is also extensible in the case that new data formats need to be supported.

The data provider 22 manages, provides access to, and in some cases transforms, normalized medical device data based on a set of services that are available to external applications. The external interface of the data provider provides access to the metrics obtained from the medical device. Each metric is tagged with a unique identifier and also includes metadata as provided by the source device, such as measurement units.

The MDIB 12 further includes a plurality of monolithic driver implementations 23, and a decorator 24 (e.g., an MDILIZER) that acquires manifest data as published per driver (or per device type) and builds the MDIB sub-tree by combining data provider 22 data and decorating it with manifest data.

Additionally, the system includes a processor 26 that executes, and a memory 28 that stores, computer-executable instructions for carrying out the various methods and actions described herein. The memory 28 may be a computer-readable medium on which a control program is stored, such as a disk, hard drive, or the like. Common forms of computer-readable media include, for example, floppy disks, flexible disks, hard disks, magnetic tape, or any other magnetic storage medium, CD-ROM, DVD, or any other optical medium, RAM, ROM, PROM, EPROM, FLASH-EPROM, variants thereof, other memory chip or cartridge, or any other tangible medium from which the processor 26 can read and execute. In this context, the system 10 may be implemented on or as one or more general purpose computers, special purpose computer(s), a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA, Graphical card CPU (GPU), or PAL, or the like.

Figure 2:
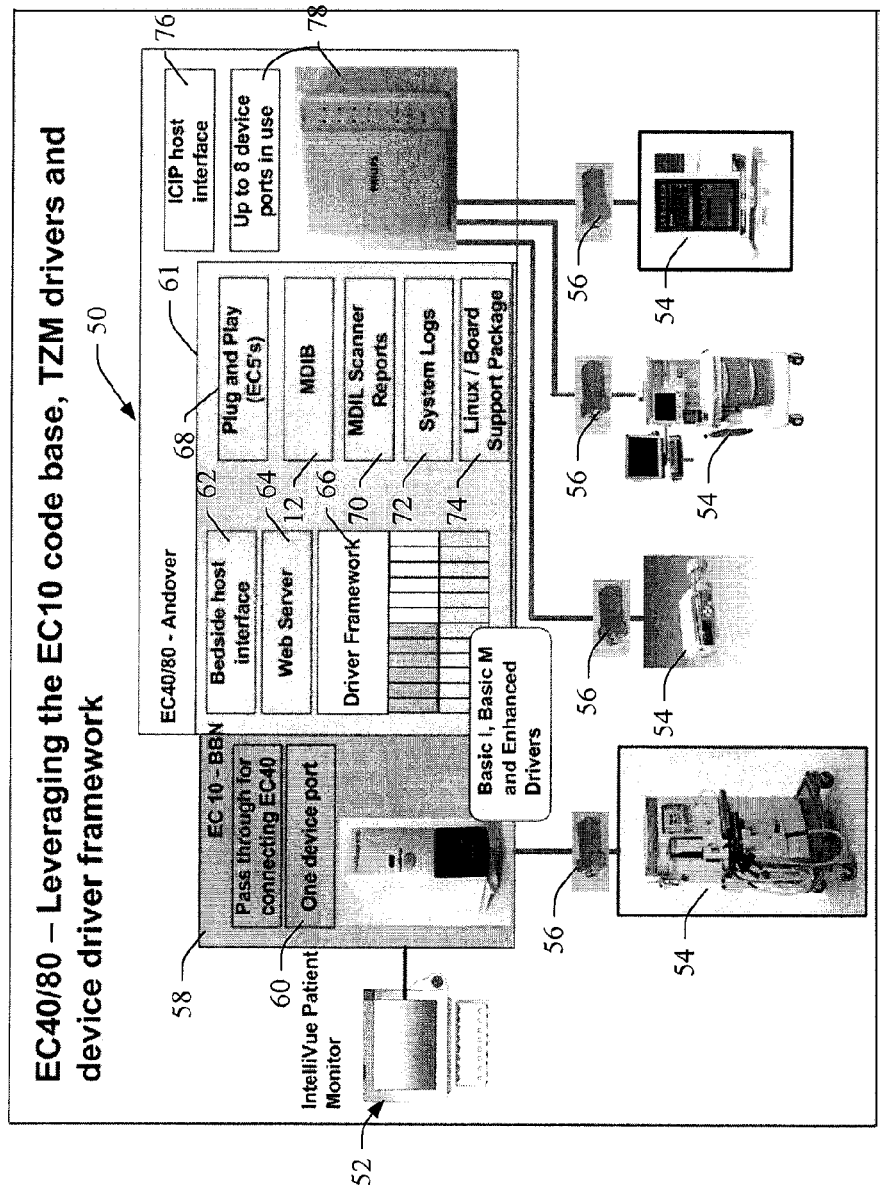
FIG. 2 illustrates a medical data acquisition device (MDAD) that leverages an EC-10 code base, associated drivers, and device driver framework.

FIG. 2 illustrates a medical data acquisition device (MDAD) 50 that leverages an EC-10 code base, associated drivers, and device driver framework. It will be appreciated that the MDAD may be coupled to or may include any or all components of the UMDDA of FIG. 1. The MDAD is coupled to a patient monitor 52, and to a plurality of medical devices 54 via respective identification modules 56. In one embodiment, the identification modules are EC-5 type modules, while the MDAD is an EC40/80 type device. The patient monitor 52 is coupled to an EC-10 BBN 58, which includes a device port 60 and acts as a pass-through connection for connecting the patient monitor to the EC-40/80 MDAD. The MDAD includes a shared code module 61, which includes computer-executable instructions that are executable using EC40/80 protocols as well as EC 10 protocols. The shared code module includes a bedside host interface 62, a web server 64, and a driver framework 66 (which may be similar or identical to the system 10 of FIG. 1) that comprises basic I, basic M, and enhanced drivers. The MDAD further includes a plug and play component (e.g., one or more EC-5 components) 68, the MDIB 12 (FIG. 1), one or more MDIL scanner reports 70, systems logs 72, and a LINUX/Board support package 74. Additionally, the MDAD includes an ICIP host interface 76 and a plurality of device ports 78 (e.g., up to 8 for EC 80).

In one embodiment, the MDAD resides in a hospital information system (HIS) that supports Health Level 7 (HL7) communication protocols. While the EC 10 communication protocol provides data for display on the monitor 52 in MDIL format, the EC 40/80 communication protocol sends the same data to the HIS for rendering in HL7 format. Thus instead of loading monolithic executables for each medical device, the MDAD finds an XML device driver file (e.g., stored on a computer-readable medium such as the memory 28 of FIG. 1) compatible with each device to communicate therewith, receive data there from, and store the data in the MDIB 12.

According to another embodiment, plug and play device drivers 68 run on the MDAD, or "hub," which obtains medical data from a device 54 and converts the received data to MDIL format and stores it in the MDIB. The ICIP host 76 converts MDIL data into HL7 format and outputs the HL7 data to the HIS.

Figure 3:
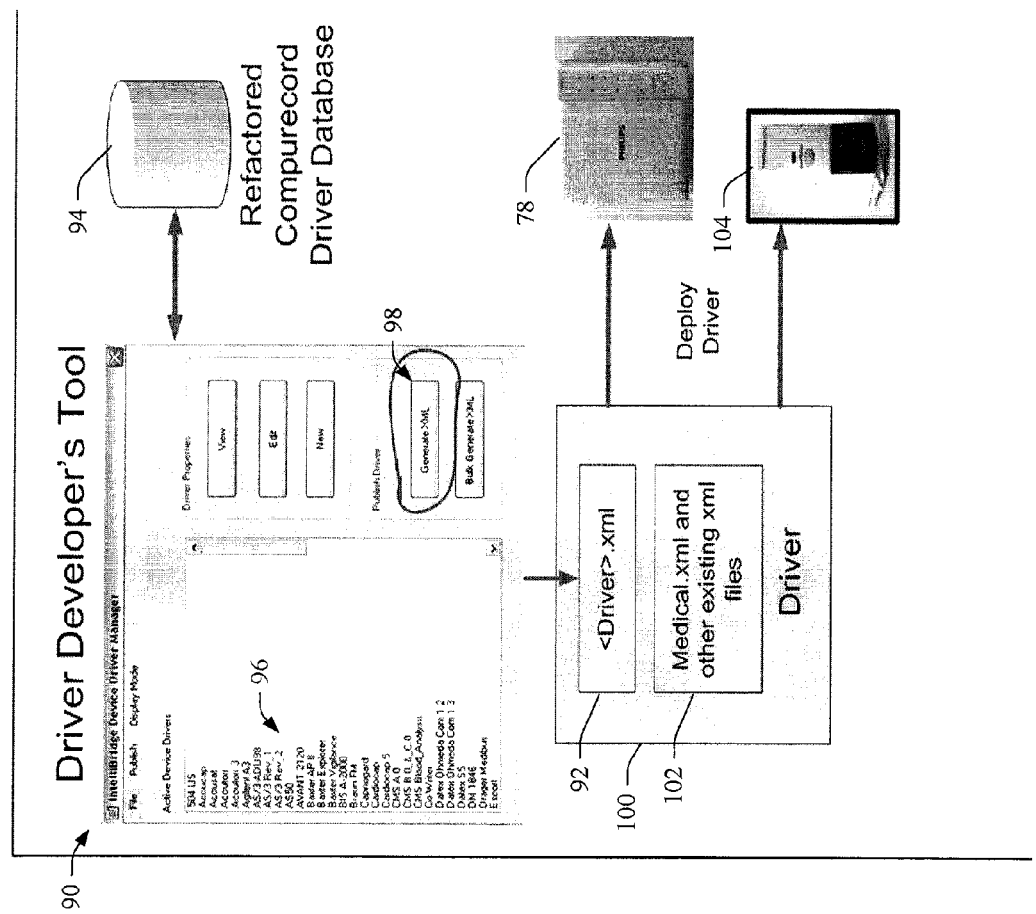
FIG. 3 illustrates a device driver manager (DDM) tool by which driver developers enter information necessary for the framework to communicate using proprietary protocols.

FIG. 3 illustrates a device driver manager (DDM) tool 90 (also called a driver developer tool herein), for use in conjunction with the UMDDA system of FIG. 1 and the MDAD 50 of FIG. 2, by which driver developers enter information necessary for the framework to communicate using proprietary protocols. The DDM tool produces an XML file 92 that embodies a model of the data that a medical device can provide as well as the device's communication capabilities. Programming skills are not needed to produce the XML file. The XML file 92 is used to configure the framework 66 (FIG. 2), and thus the framework "adapts" to the protocol supported by the medical device.

After analyzing several medical device drivers, recurring patterns may be observed in the driver software. Various design patterns can be discovered that significantly reduce driver design time and effort and maximize code reuse. An object model is created based on the design patterns. Different message parser patterns are discoverable, for example, to extract device parameters from data requests to the medical device. Examples include a "fixed length buffer parser" and a "variable length tagged buffer parser".

The DDM tool 90 stores driver configurations (e.g., XML files) to a centralized relational database 94. A user selects a device from an active device drivers (ADD) list 96 and clicks on a "Generate XML" button 98. The system generates a device driver 100 comprising the XML file 92 as well as medical.xml and other existing xml files 102. The DDM tool deploys the driver to the device 104 for which it was generated and to a device port module 78.

Figure 4:
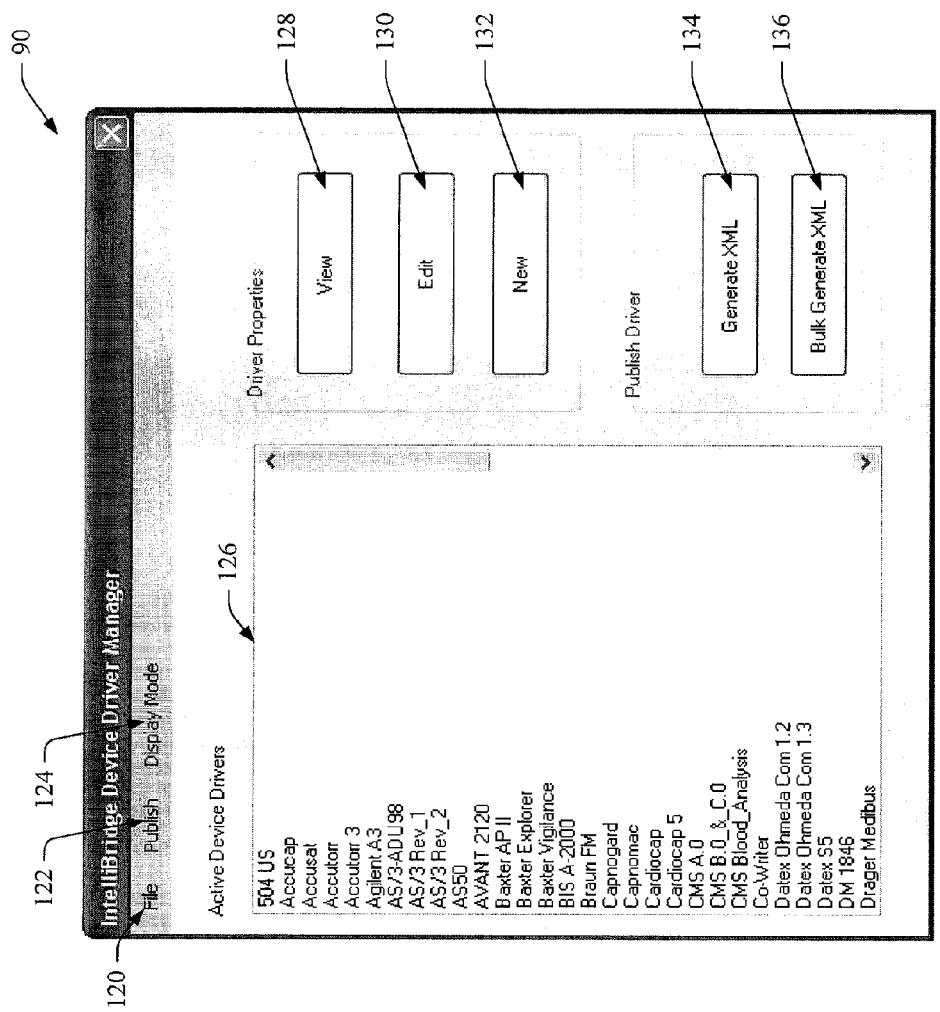
FIG. 4 illustrates a screenshot of the DDM tool, in accordance with various aspects described herein.

FIG. 4 illustrates a screenshot of the DDM tool 90, in accordance with various aspects described herein. The DDM tool is used to capture device drivers and store them during driver development as XML files in a structured query language (SQL) database, such as the relational database 94 of FIG. 3. Once the XML device driver files 92 are fully developed, they are stored in a computer-readable medium, such as the memory 28 of FIG. 1, for later recall and use. The DDM tool includes a clickable "file" tab 120, which permits a user to select a "view driver" function, an "edit driver" function, a "new driver" function, a "delete driver" function, and an "exit" function. The delete driver function removes the driver from the database, and the user is given one or more warnings prior to executing the delete command. The exit function closes the program.

The DDM tool additionally includes a clickable "publish" tab 122 that allows the user to invoke a "generate XML" function, a "bulk generate XML" function, and an "import XML" function that allows the user to import a third party device driver that conforms to the UMDDA XML file schema. Also illustrated is a "display mode" tab 124 that, when selected, determines device drivers in a list box 126. The list box 126 displays device drivers according to a selected display mode, such as "all device drivers" (e.g., active and inactive device drivers), "active device drivers," "inactive device drivers," etc.

A "View" button 128 allows the user to view all of properties on a device drive. Selecting the view button performs the same function as selecting "view driver" under the "file" tab 120. Changes to the driver are not saved when made under using the "view" function. An "Edit" button 130 allows the user to edit the properties of the device driver selected in the list box. Changes to the driver are saved to the database when the user exits the editor via an "OK" button (not shown). Selecting the edit button performs the same function as selecting the "edit driver" function under the file tab. A "New" button 132 allows the user to start the process for creating a new device driver. The device driver is saved to the database when the user exits the properties editor via an "OK" button (not shown). Selecting the new button performs the same function as selecting the "new driver" function under the file tab.

A "Generate XML" button 134 allows the user to generate an XML file for the selected device in the list box. In one embodiment, the XML file is named after the device driver in the list box and in stored at C:\IntelliBridge\DeviceDrivers. If an inactive device driver is selected, a message box is displayed and the file is not generated. The generate XML button is not active if the display mode is "inactive device drivers."

A "Bulk Generate XML" button 136 executes a function that loops through all the device drivers in the list box and creates an XML file for each one. In one embodiment, the XML files are stored at C:\IntelliBridge\DeviceDrivers. This function overwrites existing files. If the device drive is not active it is skipped. The bulk generate XML button is not active if the display mode is "inactive device drivers."

Figure 5:
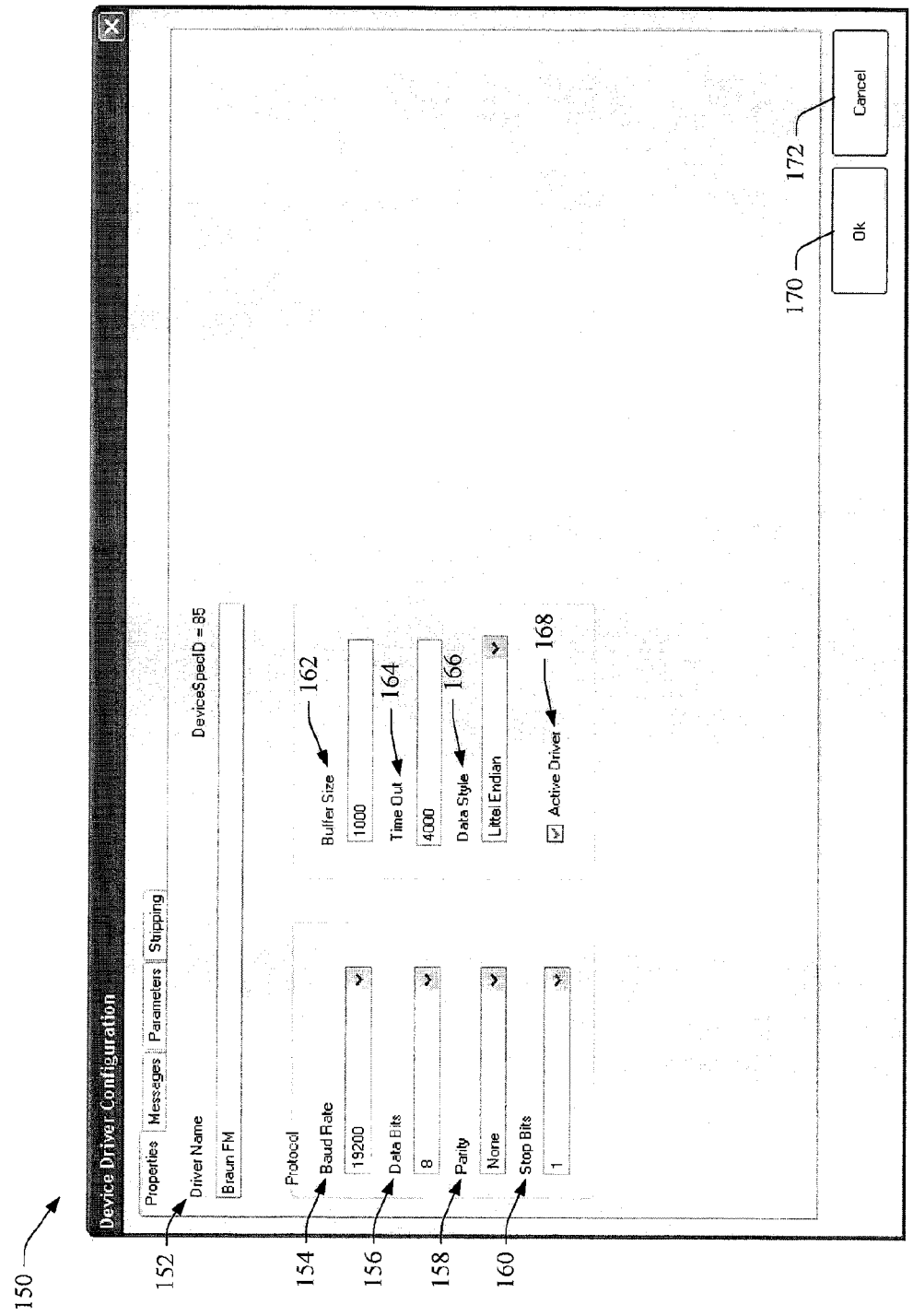
FIG. 5 illustrates a "properties" page of a device driver configuration interface (DDCI), in accordance with one or more aspects described herein.

FIG. 5 illustrates a "properties" page of a device driver configuration interface (DDCI) 150, in accordance with one or more aspects described herein. A driver name text box 152 allows the user to edit the name of a device driver. In one embodiment, the name matches a name used by the EC5 protocol, and is also used when creating an XML driver file (e.g., Braun FM.xml). A baud rate combo box 154 allows the user to set the baud rate that the driver uses for communication. This baud rate matches the baud rate of the device for which the driver is generated. In one embodiment the baud rate is in the range of approximately 300 to 115200 bps.

A "data bits" combo box 156 allows the user to set the number of data bits that are to be transmitted by the device. In one embodiment, data bit range is 5 to 8 with 8 being the most common value. A "parity" combo box 158 allows the user to set the parity checking that is to be used during communication. In one embodiment, values are None, Even, or Odd, and the selected value matches the device specification.

A "stop bits" combo box 160 allows the user to set the number of stop bits that are used for communication. In one embodiment, values can be 0, 1, 1, 5, 2, and the selected value matches the device specification. A "buffer size" text box 162 includes a value that represents the number of bytes that are available to hold the incoming message. In one embodiment, this value is at least 20% larger than the largest expected message. A "time out" text box 164 includes a value that represents the number of milliseconds that are allocated for identifying/processing an incoming message. A "data style" combo box 166 allows the user to select the format by the device when sending the raw data message. In one embodiment, values are Little Endian, Big Endian, Nibble Reverse, and user-defined. "User-defined" is a place holder and indicates an unsupported data style.

An "active driver" check box 168 allows the user to enable or disable a driver. If a driver is disabled (unchecked), then the XML file for the driver is not generated. An "OK" button 170 allows the user to exit the editor and save changes. Upon exiting, changes are saved to the SQL database. If the user entered via "View," changes are not saved. A "Cancel" button 172 allows the user to exit the editor and discard all changes.

Figure 6:
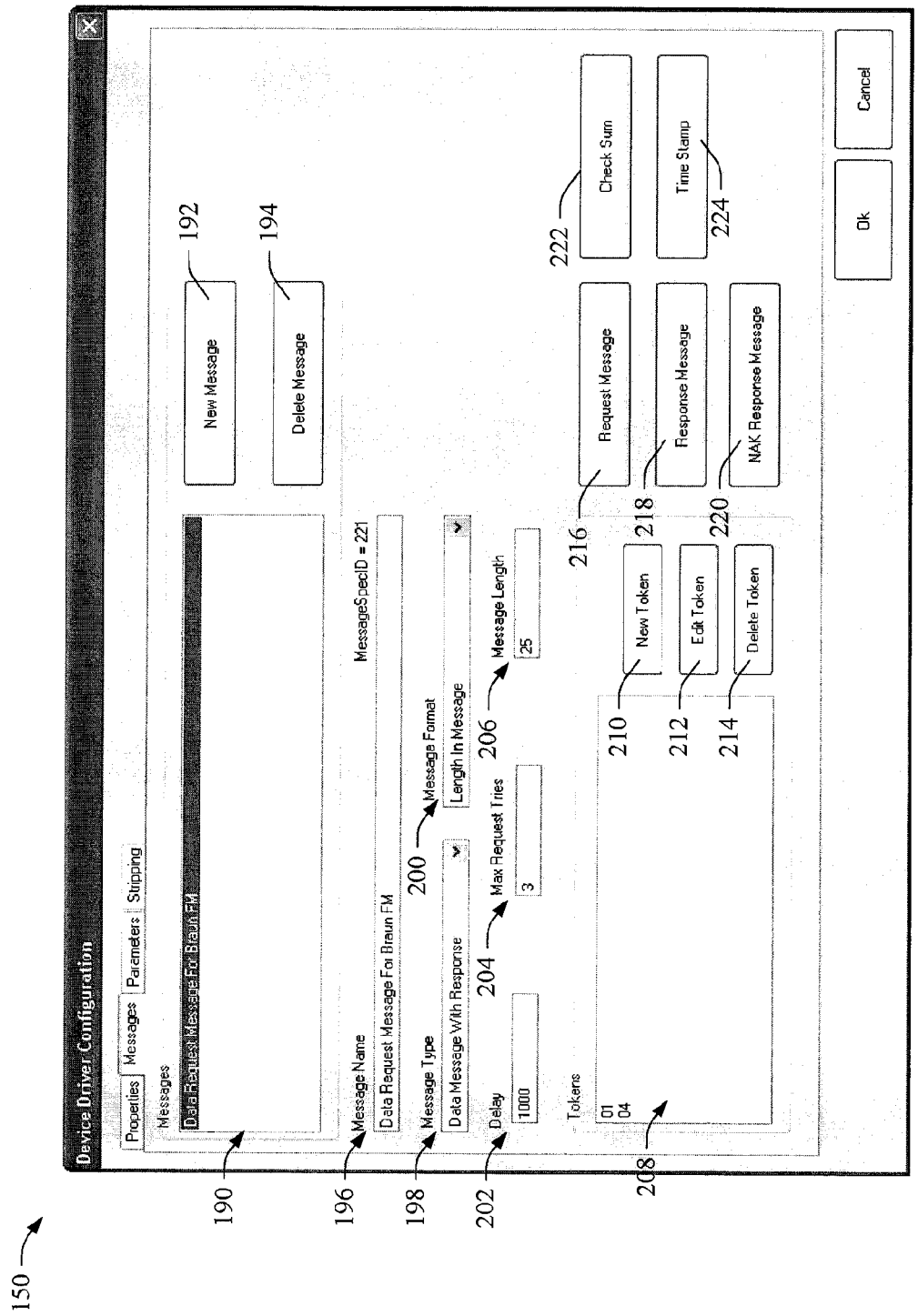
FIG. 6 illustrates a "messages" page of the DDCI, in accordance with one or more aspects described herein.

FIG. 6 illustrates a "messages" page of the DDCI 150, in accordance with one or more aspects described herein. A messages list box 190 displays the messages that are processed from a device. The properties of the selected message are displayed below. A "New Message" button 192 allows the user to add a new message to the device driver. A "Delete Message" button 194 allows the user to delete a message and all of its associated parts. A "Message Name" text box 196 is the internal name used to describe the message.

A "Message Type" combo box 198 allows the user to set the type of message that is to be processed. Message type definitions and expected uses include an "Init" (initialization) message, which is used to establish communication with the device. A "Data Message With No Response" message is a received data message that does not require a response message. A "Data Message With Response" message is a received data message that does require a response message. A "Keep Alive" or "Heartbeat" message is a message that is sent to the device to keep communication alive. An "ACK" (acknowledgement) message is a message sent to the device based on a request from the device. A "Quit" message is a message sent to the device to stop if from sending data. A "One Time Data Request" message is a request that is sent to the device which causes the device to continuously send data. Other types of messages include "Sub-message With no Response" messages, "Sub-message With Response" messages, alarm messages, etc.

A "Message Format" combo box 200 allows the user to set the method that will be used in determining the message length. A fixed length indicates that the length of the message is constant and the length is entered into the message length text box. A variable length message indicates that the length changes, and start and end tokens are needed to determine the message length. "Length in message" indicates that the length of the message can change and the exact number of bytes in the message is contained in the message. This message has a start and end token and may have a message parameter to indicate where the length can be found in the message.

A "Delay" text box 202 is provided with a value that represents the number of milliseconds that must pass before resending the request message. A "Max Request Tries" text box 204 has a value that represents the number of request tries that are preformed before a request if forced on the device regardless of the delay. A "Message Length" text box 206 includes a value that represents the number of bytes that are read in before the message search process can start. The message length text box may be set to a value which is about 10% of the typical message length.

A "Tokens" box 208 displays the tokens that are used in identifying the data message. The user is given the ability to create tokens using a "new token" button 210, edit tokens using an "edit token" button 212, or delete tokens using a "delete token" button 214. In one embodiment, tokens are displayed as hex values, such as <SOH>...<EOT>...(0x 01...0x04), etc.

A "Request Message" button 216 allows the user to view and edit the associated request. A "Response Message" button 218 allows the user to view and edit the associated response. A "NAK Response Message" 220 button allows the user to view and edit the associated NAK response. A "Check Sum" button 222 allows the user to view and edit a check sum that is associated to the message. Check sum is used to determine if the message was received correctly. A "Time Stamp" button 224 allows the user to view and edit a timestamp that is associated to the message. Timestamp is used to determine if the message is stale.

Figure 7:
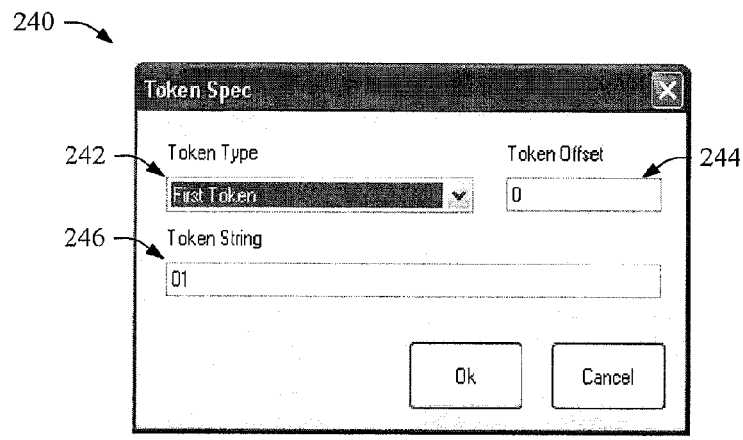
FIG. 7 illustrates a token specification editor (TSE) that facilitates generating and editing tokes that are used to identify a message, in accordance with various aspects described herein.

FIG. 7 illustrates a token specification editor (TSE) 240 that facilitates generating and editing tokens that are used to identify a message, in accordance with various aspects described herein. The TSE includes a "token type" combo field 242 that allows the user to set the token type. In one embodiment, token types include "First Token," "Message Token," and "End Token." "First token" is the first token that can be found in the message, and may be the very first byte in the message. A first token is used for message identification. There is only one first token in a message. "Message token" is any token that is found in the message. "End token" is used to identify the end of a message, and may be found at the end of a message. "End token" is used for variable length messages.

A "Token offset" text field 244 is used to indicate a location of a token in a message. The offset value is counted from the beginning of the message. An end token or first token will have an offset value of 0. A "Token String" text box 246 allows the user to enter and edit tokens in hex format. Tokens are characters that are always in the message at the same location.

Figure 8:
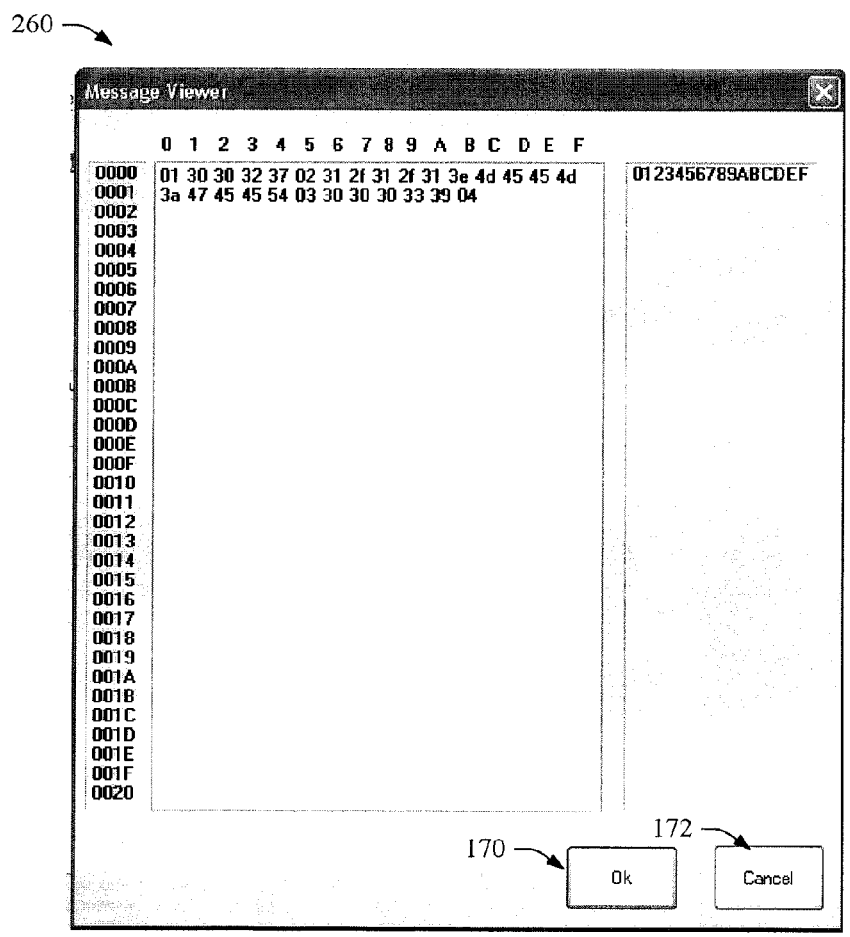
FIG. 8 illustrates a "message viewer" interface that allows a user to edit a request or response message in hex format, in accordance with one or more aspects described herein.

FIG. 8 illustrates a "message viewer" interface 260 that allows a user to edit a request or response message in hex format, in accordance with one or more aspects described herein. The user can select the "OK" button 170 to exit and save changes to the message, or can select the "Cancel" button 172 to exit without saving changes.

Figure 9:
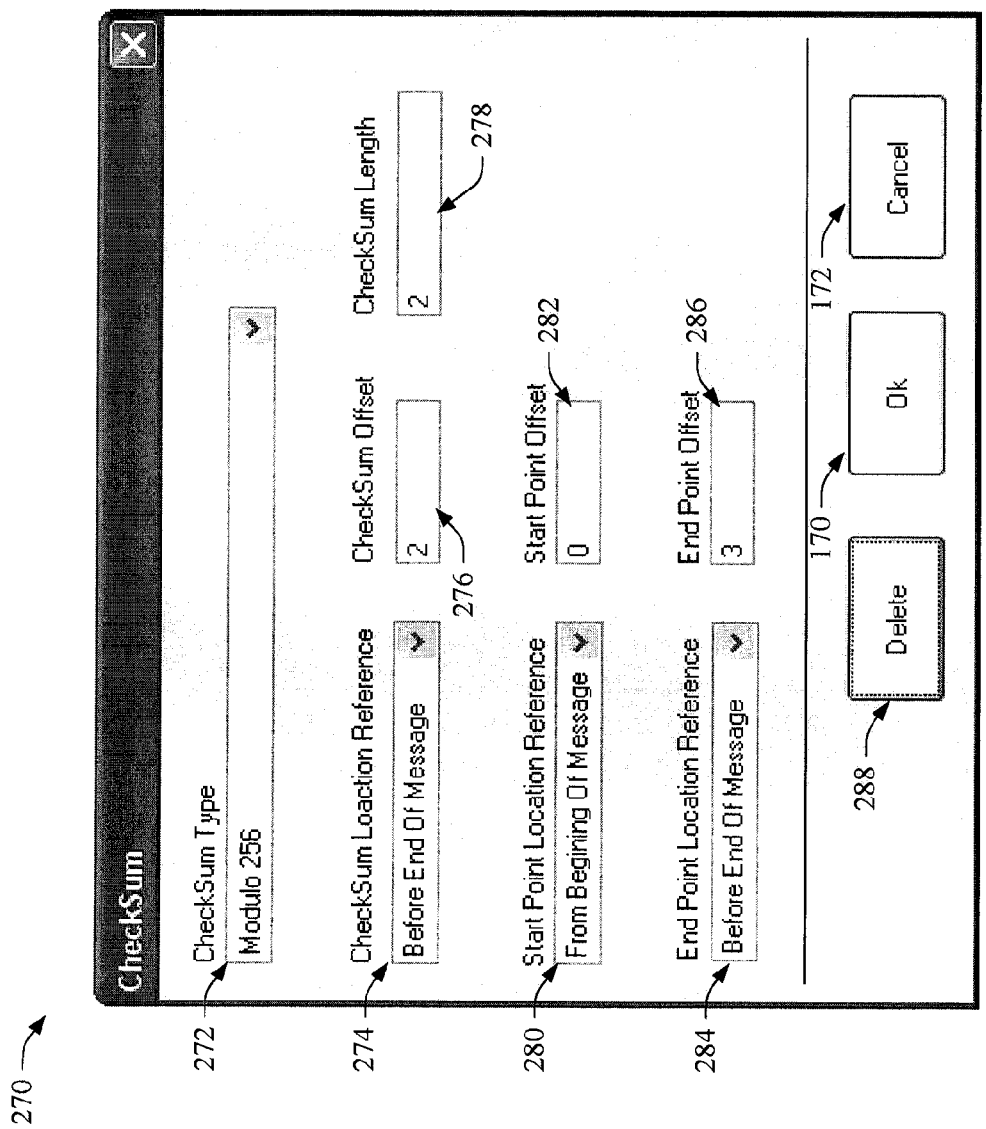
FIG. 9 illustrates a "Checksum" page or interface. A checksum is a mathematical operation applied to a number of bytes in the message.

FIG. 9 illustrates a "Checksum" page or interface 270. A checksum is a mathematical operation applied to a number of bytes in the message. The bytes exist between a start point and an end point. The start and end are included in the calculation of the checksum. The mathematical operation is determined by the "Checksum Type." Note that if a message does not have a checksum, then no checksum need be created. A "Check-Sum Type" combo box 272 allows the user to select the method that is used for calculating a checksum value. A checksum value of "None" indicates no checksum. "Byte-Sum" indicates a summation of bytes in the message. "Twos Compliment" indicates a summation of characters using a two's compliment technique. "CRC" indicates a cyclic redundancy check. "Modulo 256" indicates a sum of characters using modulo 256 addition. "User Defined" serves as a place holder and indicates that there is an unsupported checksum type.

A "CheckSum Location Reference" combo box 274 allows the user to select a starting point used in finding the check sum value in the data message. "From Beginning Of Message" in this field indicates that offset bytes will be counted from the first byte in the message. "Before End Of Message" in this field indicates that the offset bytes will be counted backwards from the last byte in the message.

A "Checksum offset" text box 276 contains a value indicative of the number of bytes that are be counted either from the start of the message of backwards from the end of the message to locate the first byte in the message's checksum value. A "Checksum length" box 278 contains a value representative of the number of bytes in the checksum value. This value may be one or two bytes in length.

A "Start Point Location Reference" combo box 280 contains a value representing the starting byte used in calculating the checksum. "From Beginning Of Message" in this field indicates that the offset bytes will be counted from the first byte in the message. "Before End Of Message" in this field indicates that the offset bytes will be counted backwards from the last byte in the message.

A "Start Point offset" text box 282 includes a value indicative of the number of bytes to be counted either from the start of the message of backwards from the end of the message to locate the start byte in the messages.

An "End Point Location Reference" combo box 284 used to point out the final byte used in calculating the checksum. "From Beginning Of Message" in this field indicates that the offset bytes will be counted from the first byte In the message. "Before End Of Message" in this field indicates that the offset bytes will be counted backwards from the last byte in the message.

An "End Point Offset" text box 286 includes a value indicative of the number of bytes to be counted either from the start of the message of backwards from the end of the message to locate the end byte in the messages. A "New 1 delete button" 288 allows the user to create or delete a check sum associated to a message. The "OK" button 170 allows the user to exit and save changes. The "Cancel" button 172 allows the user to exit without saving any changes.

Figure 10:
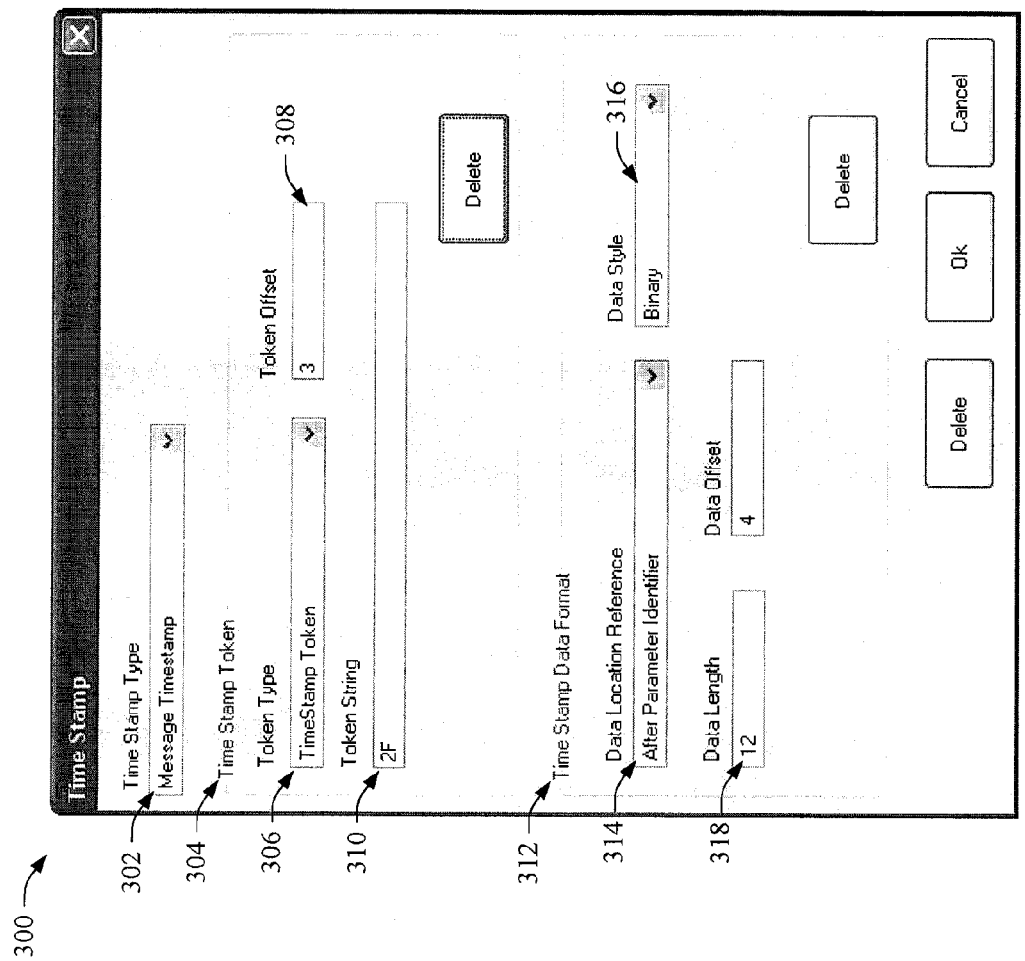
FIG. 10 illustrates a "Time Stamp" page or interface.

FIG. 10 illustrates a "Time Stamp" page or interface 300. A "Time Stamp Type" combo box 302 allows the user to select the type of time stamp that they are implementing. "Message timestamp" in this box is used to determine if the message is stale. "Parameter time stamp" in this box is used to determine if a physiological value in the message is stale. A "Time Stamp Token" field 304 is used to identify the location of the time stamp in the message. A time stamp token is optional for any type of time stamp. A "Token Type" combo box 306 allows the user to set the token type. A "Token offset" text box 308 is used to indicate where a token is located in a message. The offset value is counted from the beginning of the message. A "Token String" text box 310 allows the user to enter and edit tokens in hex format.

A "Time Stamp Data Format" field 312 is used to interpret the time stamp in the message. A "Data Location Reference" combo box 314 allows the user to select the method that is used in finding the time stamp in the message. "Beginning Of message" in this box indicates that the offset is counted from the first byte in the message, and does not require a time stamp token. "After Parameter Identifier" in this box indicates that the offset count is from the location of the first byte in the time stamp token. "Before Parameter Identifier" in this box indicates that the offset count is backwards from the location of the first byte in the time stamp token.

A "Data Style" combo box 316 determines the process for interpreting the time stamp value. In most cases binary may be used. A Data style function will perform a memory comparison to determine whether the time stamp value has changed. A "Data Length" box 318 indicates a number of bytes in the message that makes up the data.

Figure 11:
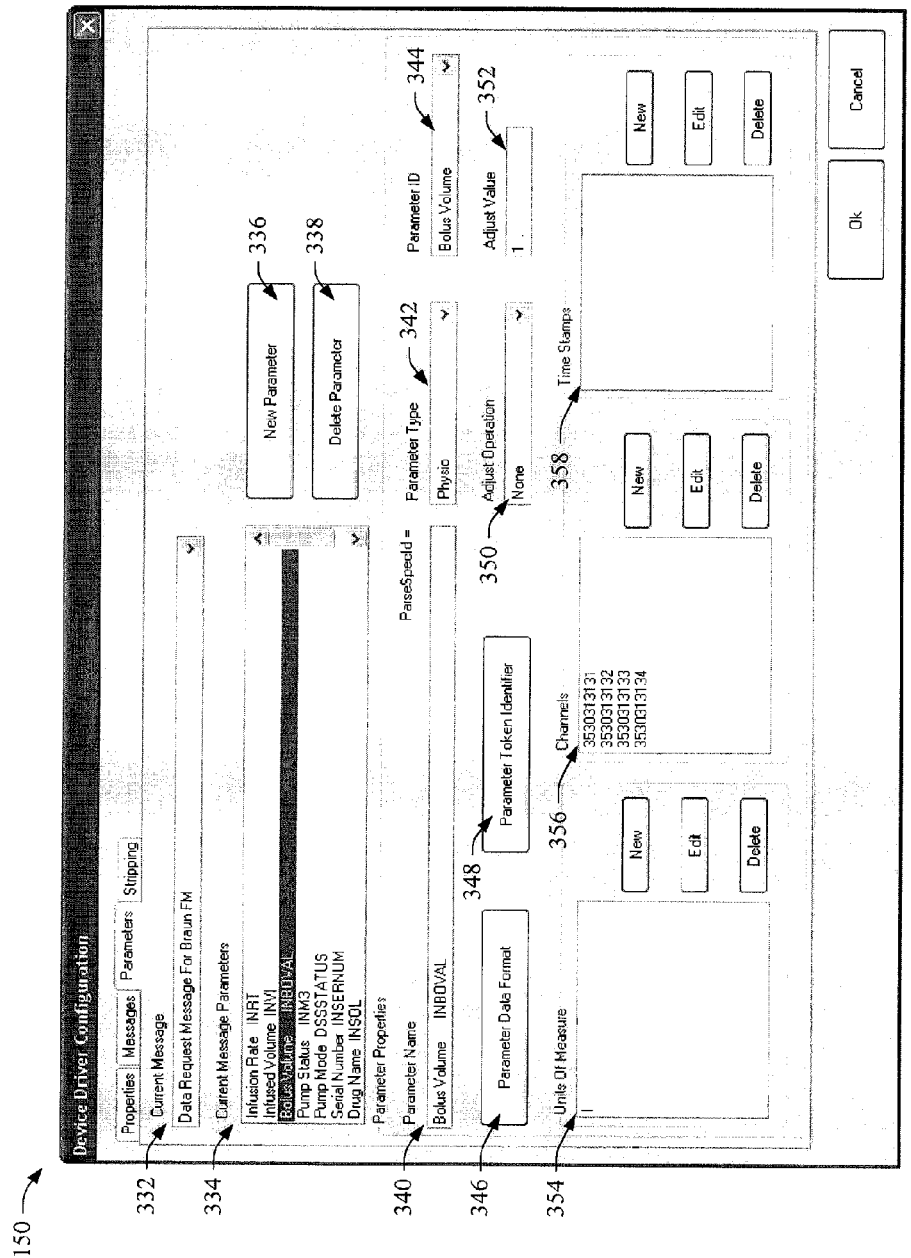
FIG. 11 illustrates a "parameters" page of the DDCI.

FIG. 11 illustrates a "parameters" page of the DDCI 150. A "Current Message" combo box 332 allows the user to select the message for which parameters are to be investigated. Selecting a message populates a "Current Message Parameters" list box 334, which displays the parameters that are associated to the message. Selecting a parameter populates the parameter properties. A "New Parameter" button 336 allows the user to create a new parameter that is associated with the current message. A "Delete Parameter" button 338 allows the user to delete a parameter and all of its associated items from the current message.

A "Parameter Name" text box 340 allows the user to edit the internal name of the parameter. A "Parameter Type" combo box 342 allows the user to select the method of parameter association. This selection determines what is loaded in a Parameter ID combo box 344. Parameter type "Physio" indicates that the parameter is associated with physio data (e.g., Heart Rate, Resp Rate, SpO2, etc.). Another parameter type may be an "Alarm" parameter. "Message Length" is a parameter is used to determine the length of the message, and may be used on a variable length message where the length information is included the message. The "Parameter ID" combo box 344 allows the user to select the data item of interest.

A "Parameter Data Format" button 346 displays a dialog allowing the user to configure the data format. A "Parameter Token Identifier" button 348 displays a dialog allowing the user to configure token that is used to identify the parameter in the message. An "Adjust operation" combo box 350 allows the user to select a mathematical operation to be applied to the raw data value. An "Adjust Value" text box 352 indicates the value used by the "adjust" operation.

A "Units Of Measure" box 354 allows the user to create a list of possible units that are associated with the parameter. If the parameter in the message has a unit of measure that is fixed, then there will only be one entry in the list. A "Channels" box 356 allows the user to create, edit, or delete a channel identifier used to identify the sub-device that the data is associated with in the message. A "Time Stamps" box 358 allows the user to create, edit, or delete a time stamp associated with the parameter. Multiple time stamps can be used if there are multiple channels. Time stamps can be applied to any periodic data elements (NIBP). Data elements that are measured continuously do not require a time stamp.

Figure 12:
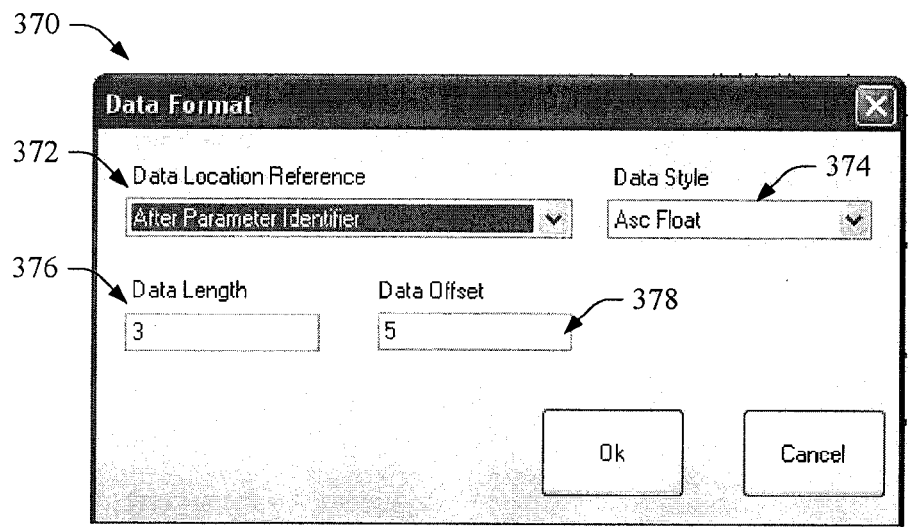
FIG. 12 illustrates a screenshot of a data format page or interface.

FIG. 12 illustrates a screenshot of a data format page or interface 370. A "Data Location Reference" combo box 372 allows the user to select the method that is used in finding the time stamp in the message. Options include "Beginning Of Message," "After Parameter Identifier," and "Before Parameter Identifier." A "Data Style" combo box 374 determines the process for interpreting the data value in the message. "Asc Int" indicates that the value is an integer in standard ASCII format (e.g., 1234=0x31 0x32 0x33 0x34). "Asc Float" indicates that the value is a float in standard ASCII format (e.g., 1234.5=0x31 0x32 0x33 0x34 0x2E 0x35). "Binary" indicates that the value is in binary format in the data message (e.g., 1234=0x04 0xD2). "String" indicates that the value in the data message is text and is in ASCII format (e.g., Format=0x46 0x6F 0x72 0x6D 0x61 0x74). "User defined" is a place holder and indicates that there is an unsupported data style. A "Data Length" text box 376 includes a number of bytes in the message that makes up the data. A "Data Offset" text box 378 shows the number of bytes to be counted to get to the location of the data.

Figure 13:
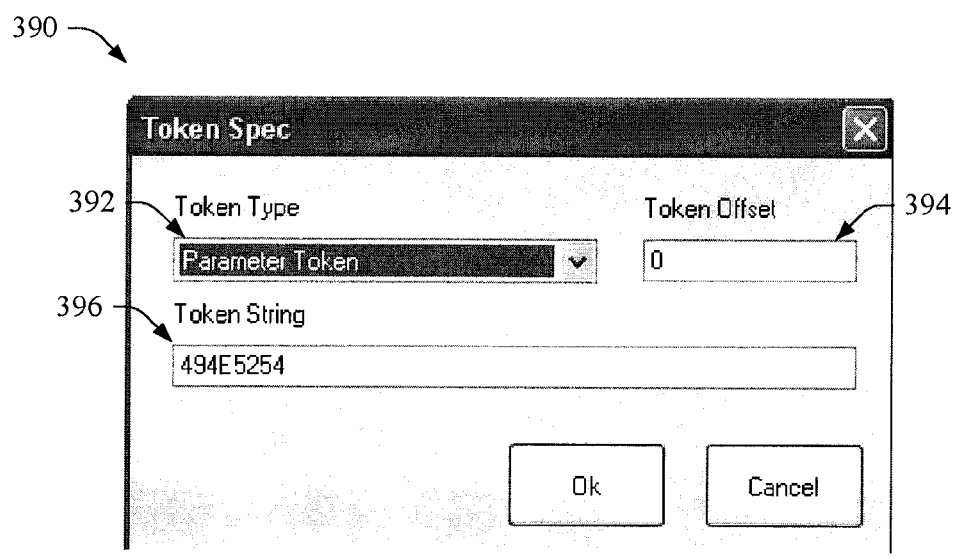
FIG. 13 is a screenshot of a token specification interface.

FIG. 13 is a screenshot of a token specification interface 390. A "Token Type" combo box 392 allows the user to set the token type. For instance, "Parameter Token" indicates that the Token is unique to the parameter and the offset is zero, forcing a search of the message for the token. "Parse Token" indicates a token that is used to delineate the message. The offset is the number of tokens that exist before the data value.

A "Token Offset" text box 394 is used to indicate where a token is located in a message. The offset value is counted from the beginning of the message. A value of zero forces a search of the message. A "Token String" text box 396 allows the user to enter and edit tokens in hex format. Tokens are unique character strings that are included the message.

Figure 14:
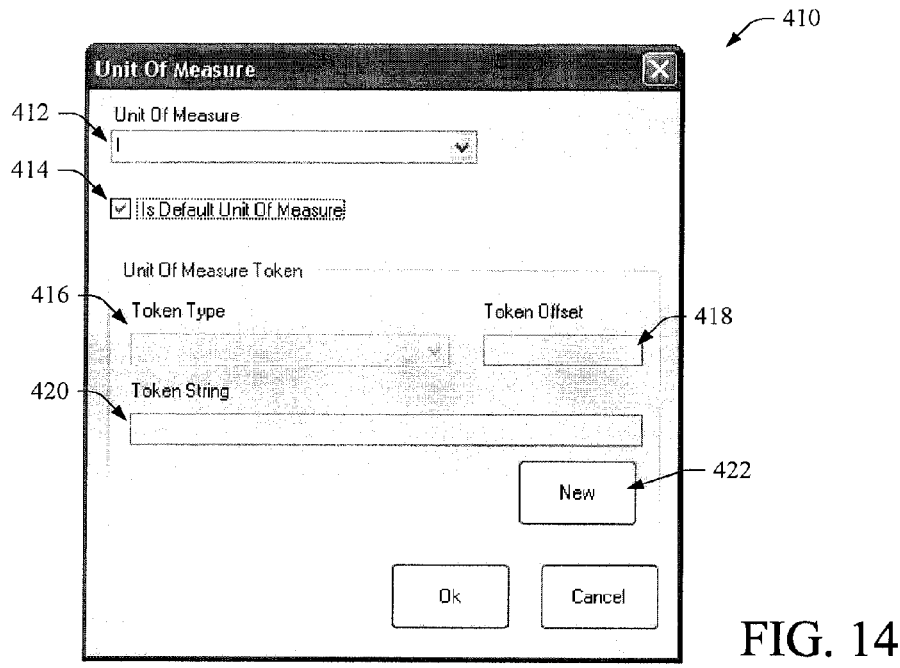
FIG. 14 is a screenshot of a "unit of measure" interface.

FIG. 14 is a screenshot of a "unit of measure" interface 410. A "Unit of Measure" combo box 412 allows a user to select a unit of measure. An "Is default unit of measure" box 414 allows a user to indicate that the selected unit of measure is the only unit of measure for the indicated parameter. A "Token Type" combo box 416 allows the user to set the token type. A "Token Offset" box 418 is used to indicate where a token is located in a message. If the message is of fixed length with no parameter identifiers, then the offset is the number of bytes from the beginning of the message. If there is a parameter identifier in the fixed length message, then the offset set is the number of bytes from the parameter identifier. If the message is variable length the offset is the maximum number of bytes needed to check past the parameter identifier for the token.

A "Token String" text box 420 allows the user to enter and edit tokens in hex format. A "New/Delete" button 422 allows the user to create or delete a token for identifying the unit of measure.

Figure 15:
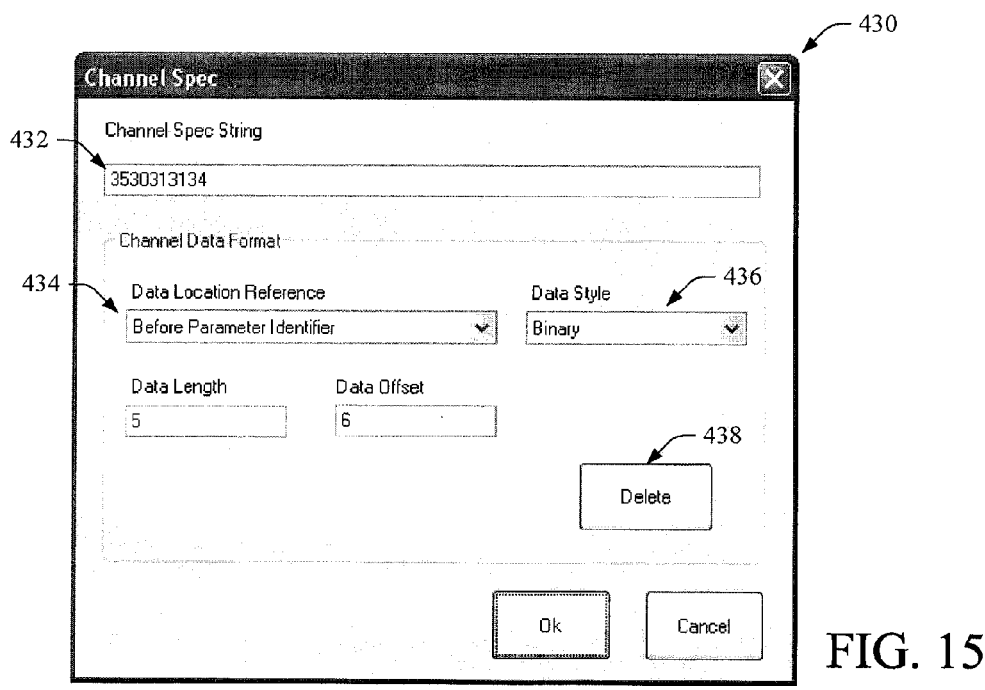
FIG. 15 is a screenshot of a channel specification interface.

FIG. 15 is a screenshot of a channel specification interface 430. A "Channel Spec String" text box 432 includes a string used to identify the parameter channel or sub device that the parameter belongs to. A "Data Location Reference" combo box 434 allows the user to select the method that is used in finding the time stamp in the message. Data location options include "Beginning Of Message," "After Parameter Identifier," and "Before Parameter Identifier." A "Data Style" text box 436 determines the process for interpreting the value. In most cases binary may be used. A "New/Delete" button 438 allows the user to create or delete a data format associated to a channel specification.

Figure 16:
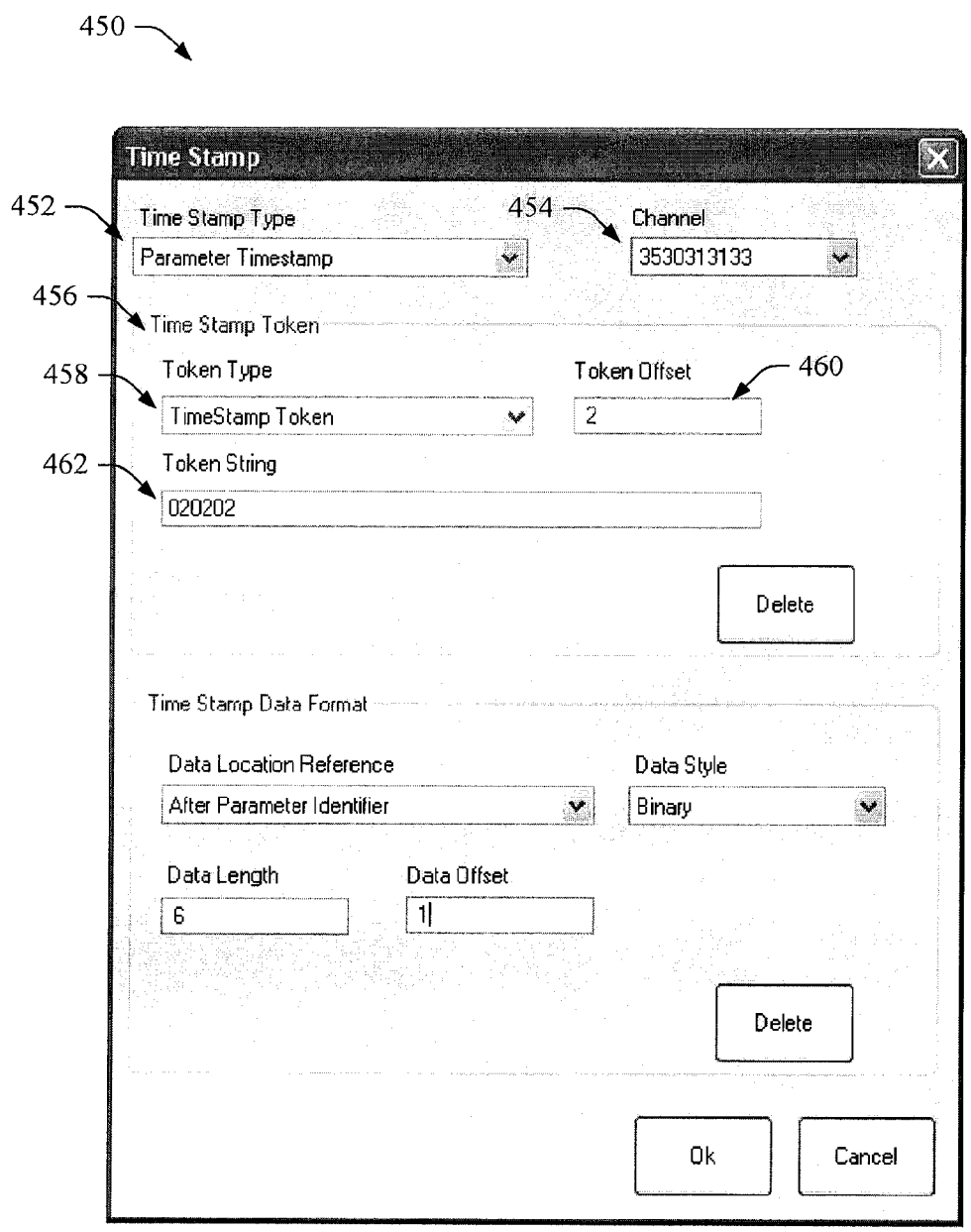
FIG. 16 illustrates a screenshot of a time stamp interface.

FIG. 16 illustrates a screenshot of a time stamp interface 450. A "Time Stamp Type" combo box 452 allows the user to select the type of time stamp being implemented. "Parameter time stamp" is used to determine if a physio value in the message is stale. A "Channel" combo box 454 allows the user to select the channel that the time stamp is to be associated with. A "Time Stamp Token" field 456 is used to identify the location of the time stamp in the message. A time stamp token is optional for any type of time stamp. A "Token Type" combo box 458 allows the user to set the token type. A "Token offset" text box 460 includes a value that is used to indicate a location of a token within a message. The offset value is counted from the beginning of the parameter identifier. A "Token String" text box 462 allows the user to enter and edit tokens in hex format.

Figure 17:
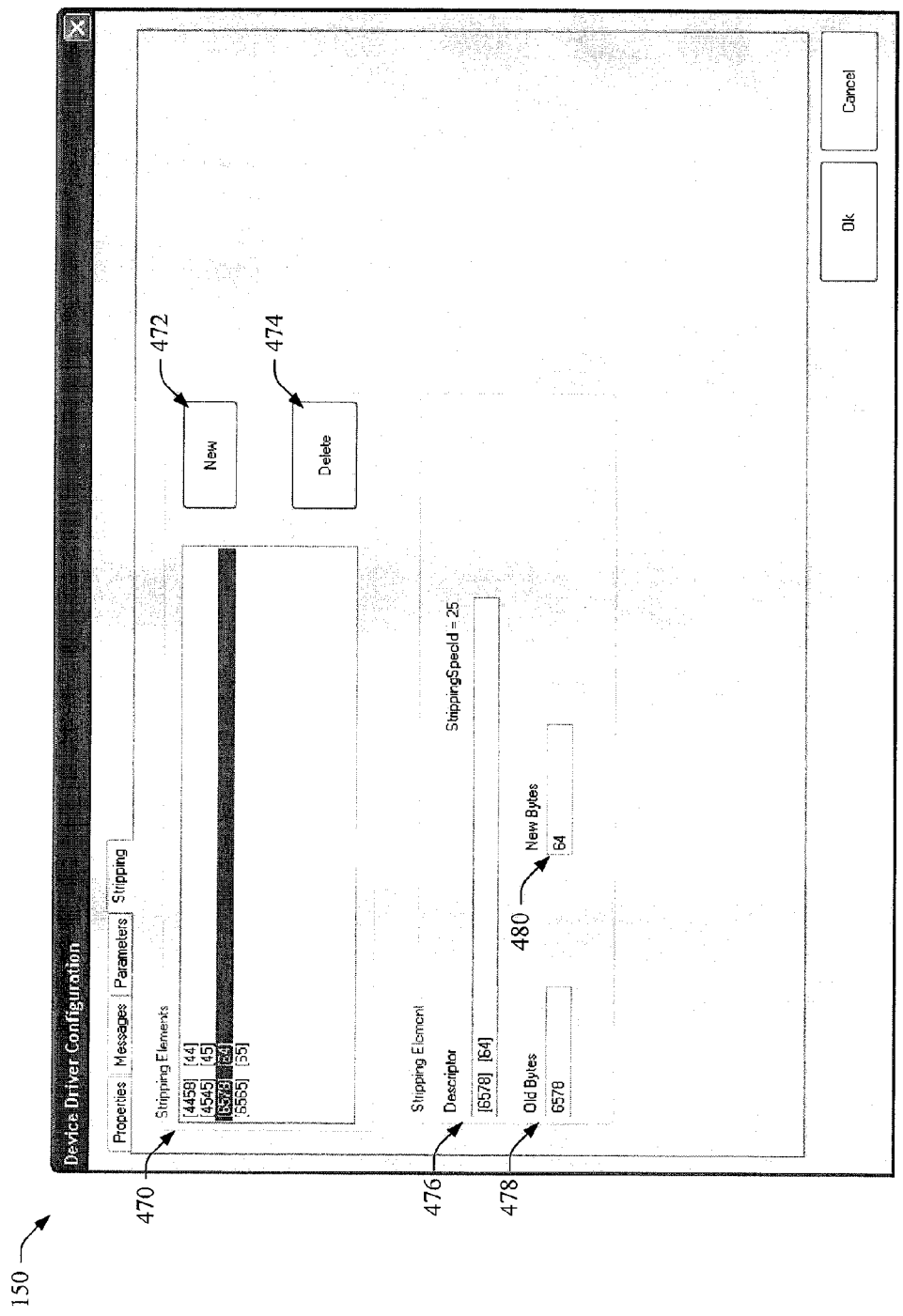
FIG. 17 is a screenshot of a "stripping page" of the DDCI.

FIG. 17 is a screenshot of a "stripping page" of the DDCI 150. A "Stripping Elements" box 470 lists the bytes that are exchanged in the message upon sending of the message. A "New" button 472 permits a user to create a new stripping spec item. A "Delete" button 474 permits a user to delete a new stripping spec item. A "Descriptor" text box 476 includes internal text used to describe the bytes and there usage. An "Old Bytes" text box 478 shows bytes that are swapped in to the message for normal bytes upon sending of the message. The bytes are represented in hex format. A "New Bytes" text box 480 shows bytes that are used to replace the old bytes in the raw data message. They must be replaced before the message is parsed. The bytes are represented in hex format.

Figure 18:
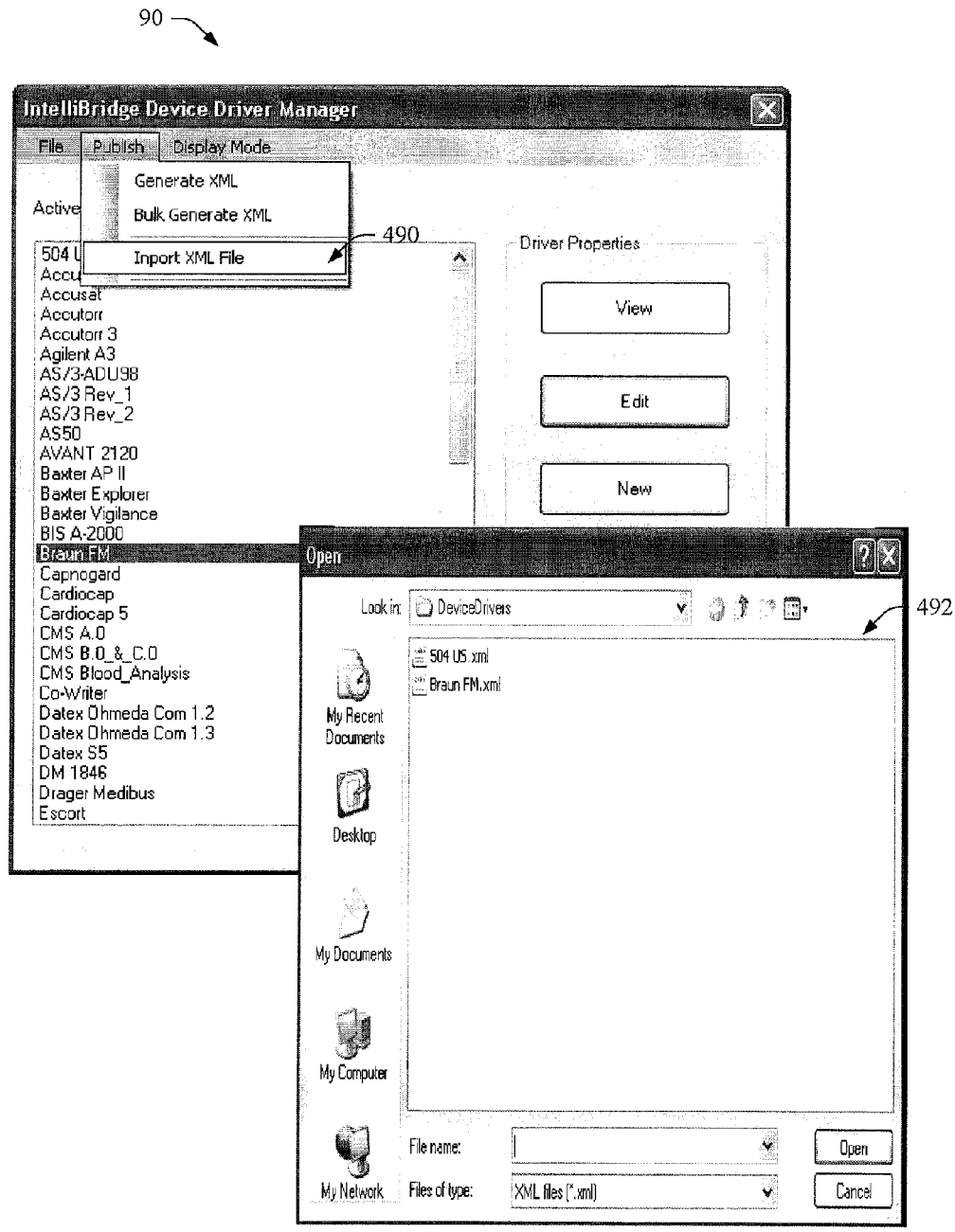
FIG. 18 is a screenshot of the device driver manager in which an "Import XML File" option has been selected form a drop down menu.

FIG. 18 is a screenshot of the device driver manager 90 in which an "Import XML File" option 490 has been selected form a drop down menu. The Import XML File function allows a user to import a device driver that was created by a third party and add the device driver to the master database of device drivers. The user is presented with an open file dialog 492 in which they can select the driver that they wish to import. When importing a driver, the user is given the option of reviewing the driver in the editing tool or directly importing it to the database. If reviewing the driver before importing, the driver is loaded into the editor for the user to review. If the user exits the editor via cancel the driver is not saved to the database.

For example, the DDM tool described herein can be provided to a manufacturer of a medical device that will ultimately be coupled to the described system(s). The manufacturer can generate an XML file for the device, which can then be imported to the SQL database 94 (FIG. 3) by selecting the "Import XML File" option. In this manner, the manufacturer need not disclose proprietary information associated with the device.

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

Having thus described the preferred embodiments, the invention is now claimed to be:

1. A system that facilitates providing reusable code for device drivers in an expandable and scalable framework, including:
   a multi-port medical data acquisition device (MDAD) that detects a medical device coupled to the MDAD via a single port pass-through connection;
   a device driver manager (DDM) tool that generates a reusable plug-and-play extensible markup language (XML) device driver file for the medical device by:
      selecting a device driver from a list of device drivers;
      configuring an XML device driver file for the selected device driver;
      generating the reusable plug-and-play XML device driver file when it is completely configured; and
   computer-readable medium that stores the reusable plug-and-play XML device driver file for use whenever the medical device or a similar device is coupled to the system;
   wherein the reusable plug-and-play XML device driver file includes a plurality of format parameters descriptive of a device driver for the medical device.

2. The system according to claim 1, further including:
   a patient monitor coupled to the MDAD via the single-port pass-through connection.

3. The system according to claim 2, further including:
   a shared code module that includes code usable by the single-port pass-through connection and the multi-port MDAD.

4. The system according to claim 1, wherein the format parameters include at least one of:
   driver name;
   baud rate;
   parity;
   buffer size;
   time stamp information;
   token information;
   data style;
   stop bit information; and
   message information.

5. The system according claim 1, wherein the MDAD retrieves from the computer-readable medium an XML file compatible with the medical device, loads the XML file into a driver framework in order to communicate with and receive data from the medical device, and stores the received data in a medical data information base (MDIB).

6. The system according to claim 5, further including:
   an ICIP host that converts received data from an MDIL format to a Health Level 7 (HL7) format and outputs the HL7-formatted data to a hospital information system (HIS).

7. A processor configured to execute a method of generating reusable extensible markup language (XML) device driver files, the method being stored as a set of computer-executable instructions on a non-transitory computer-readable medium and including:
   selecting a device driver from a list of device drivers;
   configuring an XML device driver file for the selected device driver using a device driver manager (DDM) tool;
   generating the XML device driver file when it is completely configured; and
   storing the generated XML device driver file to a computer-readable medium for recall upon detection of a compatible medical device;
   wherein the generated XML device driver file includes a plurality of format parameters descriptive of a device driver for a medical device.

8. The processor according to claim 7, the instructions further including:
   detecting a plug-in event for a newly-connected medical device;
   receiving medical device driver information descriptive of the medical device;
   retrieving a compatible XML device driver file from the computer-readable medium; and
   executing the retrieved XML device driver in order to communicate bidirectionally with the newly-connected medical device.

9. The processor according to claim 7, wherein configuring the XML device driver file includes configuring:
   one or more driver properties;
   one or more message properties;
   one or more driver parameters; and
   one or more stripping elements.

10. The processor according to claim 9, wherein the one or more driver properties include at least one of:
   a driver name;
   a baud rate;
   a number of data bits;
   a parity value;
   a stop bit value;
   a buffer size;
   a timeout value;
   and a data style indicator.

11. The processor according to claim 9, wherein the one or more message properties include at least one of:
- a message name;
- a message type;
- a message format;
- a delay value;
- a maximum number of requests;
- a message length;
- token information;
- timestamp information; and
- checksum information.

12. The processor according to claim 9, wherein the one or more driver parameters include:
- current message identity;
- current message parameters; and
- parameter property information.

13. The processor according to claim 12, wherein the parameter property information includes at least one of:
- a parameter name;
- a parameter type;
- a parameter identity;
- a parameter adjust operation information;
- a parameter adjust value;
- unit of measure information;
- parameter communication channel information;
- and parameter timestamp information.

14. The processor according to claim 9, wherein the one or more stripping elements include at least one of:
- descriptor information;
- a number of old bytes;
- and a number of new bytes.

15. The processor according to claim 7, the instructions further including:
- importing an XML device driver file created by a third party manufacturer and compatible with one or more medical devices manufactured by the third party manufacturer; and
- storing the imported XML device driver file to the computer-readable medium for recall upon detection of a medical device manufactured by the third party manufacturer.

16. A non-transitory computer-readable medium having stored thereon an extensible markup language (XML) device driver manager (DMM) tool, including:
- a user interface that includes a plurality of selectable buttons and text fields by which a user enters information and configures an XML device driver file for a medical device, the information including:
  - one or more driver properties;
  - one or more message properties;
  - one or more driver parameters; and
  - one or more stripping elements.

17. The non-transitory computer-readable medium according to claim 16, wherein;
- the computer-readable medium stores a plurality of XML device driver files;
- wherein the DMM tool retrieves an XML device driver file for a compatible medical device upon detection of a plug-and-play event whereby the compatible medical device becomes connected to a hospital information system (HIS) to which the DMM tool is connected.

* * * * *